United States Patent
Kang et al.

(10) Patent No.: US 9,650,604 B2
(45) Date of Patent: May 16, 2017

(54) EQUINE AMNIOTIC MEMBRANE-DERIVED MESENCHYMAL STEM CELLS

(71) Applicant: Kang Stem Biotech, Co., LTD., Seoul (KR)

(72) Inventors: Kyung Sun Kang, Seoul (KR); Min Soo Seo, Daegu (KR); Sang Bum Park, Seoul (KR)

(73) Assignee: Kang Stem Biotech, Co., LTD., Seoul (KR)

( * ) Notice: Subject to any disclaimer, the term of this patent is extended or adjusted under 35 U.S.C. 154(b) by 0 days.

(21) Appl. No.: 14/359,974

(22) PCT Filed: Nov. 22, 2012

(86) PCT No.: PCT/KR2012/009903
§ 371 (c)(1),
(2) Date: May 22, 2014

(87) PCT Pub. No.: WO2013/077639
PCT Pub. Date: May 30, 2013

(65) Prior Publication Data
US 2014/0335060 A1    Nov. 13, 2014

(30) Foreign Application Priority Data

Nov. 22, 2011 (KR) ......................... 10-2011-0122548

(51) Int. Cl.
*A61K 35/50* (2015.01)
*C12N 5/074* (2010.01)
*C12N 5/0775* (2010.01)

(52) U.S. Cl.
CPC ............ *C12N 5/0607* (2013.01); *A61K 35/50* (2013.01); *C12N 5/0668* (2013.01); *C12N 2500/24* (2013.01); *C12N 2500/32* (2013.01); *C12N 2500/34* (2013.01); *C12N 2500/38* (2013.01); *C12N 2501/00* (2013.01); *C12N 2501/33* (2013.01); *C12N 2506/03* (2013.01)

(58) Field of Classification Search
CPC C12N 5/0607; C12N 5/0668; C12N 2506/03; C12N 2506/1392; A61K 35/50
See application file for complete search history.

(56) References Cited

U.S. PATENT DOCUMENTS

2009/0238801 A1*   9/2009   Woodbury et al. .......... 424/93.7

FOREIGN PATENT DOCUMENTS

| KR | 100795708 B1 | 1/2008 |
|---|---|---|
| KR | 100818214 B1 | 3/2008 |

OTHER PUBLICATIONS

Miki et al., Stem cell characteristics of amniotic epithelial cells. Stem Cells, vol. 23, No. 10 (Nov. 2005) pp. 1549-1559.*
Kim et al., Ex vivo characteristics of human amniotic membrane-derived stem cells. Cloning and Stem Cells, vol. 9, No. 4 (2007) pp. 581-594.*
11885-DMEM, low glucose, pyruvate. Datasheet [online]. ThermoScientific, 2015 [retrieved on Dec. 28, 2015]. Retrieved from the Internet: <URL: http://www.thermofisher.com/us/en/home/technical-resources/media-formulation.48.html>.*
Carvalho, et al "Isolation and immunophenotypic characterization of mesenchymal stem cells derived from equine species adipose tissue," Veterinary Immunology and Immunopathology 132 (2009) 303-306.
Verfaillie, Catherine M. "Adult stem cells: assessing the case for pluripotency" Trends in Cell Biology vol. 12 No. 11 Nov. 2002 502-508.
Coli, et al "Isolation and characterization of equine amnion mesenchymal stem cells" Cell Biol Int Rep (2011) 18, 23-29.
Park, et al "Isolation and characterization of equine amniotic fluid-derived multipotent stem cells" Cytotherapy, 2011; 13: 341-349.
Sampaolesi et al "Cell Therapy of a-Sarcoglycan Null Dystrophic Mice Through Intra-Arterial Delivery of Mesoangioblasts" Science vol. 301 Jul. 25, 2003 487-492.
Ariffin, Shahrul Hisham Zainal et al., "Differentiation of Dental Pulp Stem Cells into Neuron-Like Cells in Serum-Free Medium" Hindawi Publishing Corporation, Stem Cells International, vol. 2013, Article ID 250740, 10 pages http://dx.doi.org/10.1155/2013/250740.
Cheng, Nai-Chen et al., "High glucose-induced reactive oxygen species generation promotes sternness in human adipose-derived stem cells" Cytotherapy, 2016; 18: 371-383.
Lee, Kuan-Der et al., "In Vitro Hepatic Differentiation of Human Mesenchymal Stem Cells" Hepatology, Dec. 2004, vol. 40, No. 6, pp. 1275-1284.

* cited by examiner

*Primary Examiner* — Kara Johnson
(74) *Attorney, Agent, or Firm* — Edwin S. Flores; Daniel J. Chalker; Chalker Flores, LLP

(57) ABSTRACT

The present invention relates to equine amniotic membrane-derived mesenchymal stem cells (eAM-MSCs) and a preparation method thereof. More specifically, the present invention relates to equine amniotic membrane-derived mesenchymal stem cells, which show negative immunological responses to all of the human markers CD19, CD20, CD28, CD31, CD34, CD38, CD41a, CD62L, CD62P and CD200, and positive immunological responses to all of the human markers CD44, CD90 and CD105, and have the ability to be maintained in an undifferentiated state for 14 passages or more and the ability to differentiate into ectoderm, mesoderm and endoderm-derived cells.

14 Claims, 5 Drawing Sheets

Figure 1
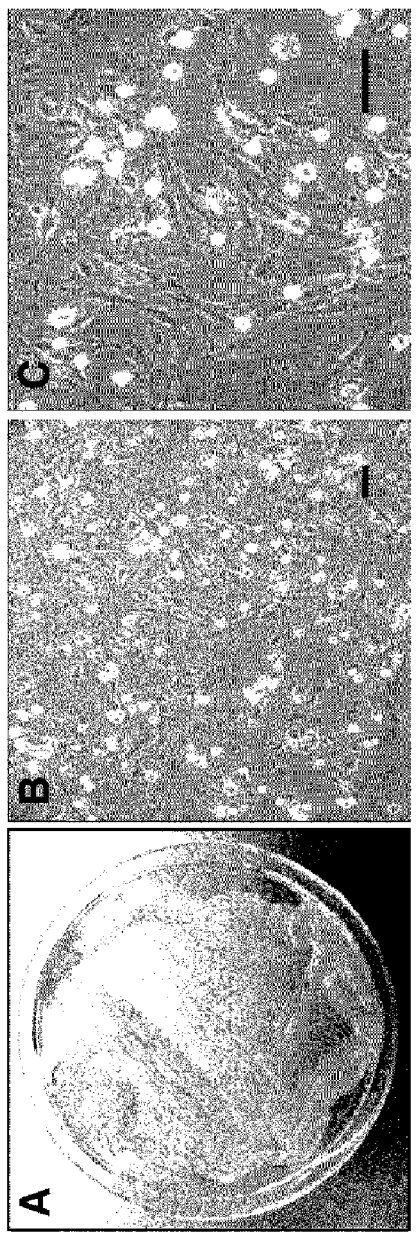
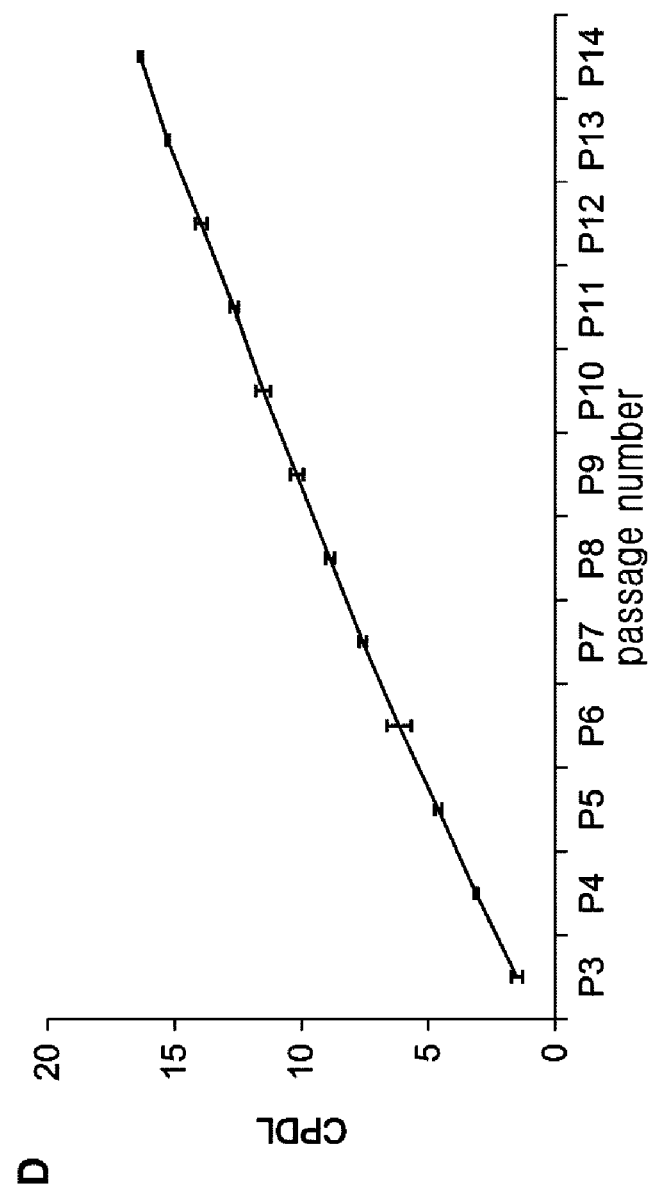

EQUINE AMNIOTIC MEMBRANE-DERIVED MESENCHYMAL STEM CELLS

CROSS-REFERENCE TO RELATED APPLICATIONS

This application is the National Stage of International Application No. PCT/KR2012/009903, filed on 22 Nov. 2011 claiming the priority of KR 10-2011-0122548 filed on 12 Oct. 2011, the content of each of which is incorporated by reference herein.

TECHNICAL FIELD

The present invention relates to equine amniotic membrane-derived mesenchymal stem cells (eAM-MSCs) and a preparation method thereof. More specifically, the present invention relates to equine amniotic membrane-derived mesenchymal stem cells, which show negative immunological responses to all of the human markers CD19, CD20, CD28, CD31, CD34, CD38, CD41a, CD62L, CD62P and CD200, and positive immunological responses to all of the human markers CD44, CD90 and CD105, and have the ability to be maintained in an undifferentiated state for 14 passages or more and the ability to differentiate into ectoderm, mesoderm and endoderm-derived cells.

BACKGROUND ART

Biotechnology in the 21$^{st}$ century presents the possibility of new solutions to food, environment and health problems, with the ultimate object of promoting human prosperity. In recent years, the technology of using stem cells has been considered as a new way to treat incurable diseases. Formerly, organ transplantation, gene therapy, etc., were proposed for the treatment of incurable human diseases, but their use has not been achieved efficiently due to immunorejection, a small supply of organs, and insufficient knowledge of genes.

For this reason, with increasing interest in stem cell research, it has been recognized that totipotent stem cells having the ability to form all organs by proliferation and differentiation can not only treat most diseases but also fundamentally heal organ injuries. Also, many scientists have suggested the applicability of stem cells for the regeneration of all the organs and the treatment of incurable diseases, including Parkinson's disease, various cancers, diabetes and spinal damage.

Stem cells refer to cells having not only self-replicating ability but also an ability to differentiate into at least two types of cells, and can be divided into totipotent stem cells, pluripotent stem cells, and multipotent stem cells (MSCs).

Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual. Pluripotent stem cells, which are cells capable of developing into various cells and tissues derived from the ectodermal, mesodermal and endodermal layers, are derived from an inner cell mass located inside of blastocysts generated 4-5 days after fertilization. These cells are also called embryonic stem cells and can differentiate into various other tissue cells but cannot form new living organisms.

Multipotent stem cells were first isolated from adult bone marrow (Y. Jiang et al., *Nature*, 418: 41, 2002), and then also found in other various adult tissues (C. M. Verfaillie, *Trends Cell Biol.*, 12: 502, 2002). In other words, although the bone marrow is the most widely known source of stem cells, the multipotent stem cells were also found in the skin, blood vessels, muscles and brains (J. G. Tomas et al., *Nat. Cell Biol.*, 3: 778, 2001; M. Sampaolesi et al., *Science*, 301: 487, 2003; Y. Jiang et al., *Exp. Hematol.*, 30: 896, 2002). However, stem cells in adult tissues, such as the bone marrow, are very rarely present, and such cells are difficult to culture without inducing differentiation, and thus difficult to culture in the absence of specifically screened media.

The reason why it is important to establish cell lines of such multipotent stem cells is because of the objectives of the research on the proliferation, lyophilization and characterization of stem cell lines, drug tests, and the autologous, allogeneic and xenogeneic transplantation of stem cell lines.

The equine is a mammal belonging to the Equidae (Genus *Equus*), and is one of the rare types of animals that have been domesticated by humans, along with dogs or cats. Equine industries, including the horse racing industry, are growing worldwide. In the horse racing industry, racehorses with a good pedigree are highly valuable. When such racehorses with a good pedigree are injured, the healing of the racehorses is problematic. Thus, the development of cell therapy for equine animals has received attention. Considering the size of horses, it is a major technical issue to reliably supply a large number of cells.

Therefore, isolation and characterization of stem cells derived from various equine tissues have become important issues in the stem cell field. Conventionally, there have been studies on stem cells from human and mouse tissues in various fields. However, studies on cell therapeutic agents for the treatment of bone, cartilage, tendon or muscle of equine animals, in particular racehorses, have not yet been sufficient, even though the need for the cell therapeutic agents is great.

There was a report on the isolation of stem cells from equine adipose tissues (Armando de Mattos Carvalho et al., *Veterinary Immunology and Immunopathology*, 132: 303, 2009). However, equine animals do not have much adipose tissue, unlike other mammals, and thus it is very difficult to obtain adipose tissue from equine animals. In addition, a method of obtaining adipose from individuals is invasive and causes pain. In the case of stem cells from equine bone marrow, the isolation of bone marrow is also performed using an invasive method, like that used for obtaining adipose. Also, due to the nature of racehorses, there is a distinct limitation in the isolation of stem cells from adipose tissue or bone marrow.

In the current state of technology, in order to use adult stem cells as cell therapeutic agents, it is required to standardize the culture conditions under which an undifferentiated state can be maintained. In addition, because adult stem cells isolated from tissues are present as a mixture of various kinds of cells, it is required to develop technology capable of culturing homogeneous adult stem cells on a mass scale. In particular, methods for isolating adult stem cells from tissues or blood generally include, for example, cell sorting utilizing antibodies for a number of surface antigens. However, this method has a shortcoming in that the surface antigens of adult stem cells should be known. In addition, a common surface antigen (hereinafter referred to as "marker") for adult stem cells is not yet known. Also, various markers for adult stem cells have not been developed, and known markers for adult stem cells are expressed at different levels depending on the differentiation state of adult stem cells. Particularly, a system of sorting cells according to the expression level of the markers is expensive. Due to such shortcomings, the use of the cell sorting method has been greatly limited.

The placenta plays an important role in the development and survival of a fetus by supplying nutrients and oxygen thereto. Generally, the placenta is disposed of as medical waste after delivery. However, recent studies indicate that human amniotic tissue is a source rich in stem cells, and many studies on stem cells derived therefrom have been conducted. In clinical applications, amniotic tissue has effects on wound healing and retinal reconstitution. The amnion may possibly contain stem cells in a mixture with other monocytes and other stem cells. Under culture conditions for such mixed cells, the distribution of nutrients cannot be uniform, thereby causing heterogeneity in differentiation of cells. Conclusively, the problem that the cells cannot be produced as a homogeneous cell population serves as a fatal disadvantage, as when they are used as the therapeutic agent the actual effect may be different from the intended effect. Therefore, there is an urgent need for the development of effective culture technology that makes it possible to obtain homogeneous adult stem cells in a large quantity.

DISCLOSURE

Technical Problem

The present inventors first isolated a population of stem cells having increased homogeneity from an equine amniotic membrane, which is a new source of stem cells and is easily collected from female horses after delivery. They have found that the isolated stem cells have more rapid and continuous self-renewal (growth ability) than other stem cells and show the immunological characteristics of mesenchymal stem cells and have an excellent multilineage differentiation capability, thereby completing the present invention.

Technical Solution

It is an object of the present invention to provide equine amniotic membrane-derived mesenchymal stem cells.

Another object of the present invention is to provide a method for preparing equine amniotic membrane-derived mesenchymal stem cells.

Still another object of the present invention is to provide a method for differentiating equine amniotic membrane-derived mesenchymal stem cells into various types of cells.

Still another object of the present invention is to provide a cell therapeutic agent containing equine amniotic membrane-derived mesenchymal stem cells or the tissue cells differentiated therefrom, as an active ingredient.

Still another object of the present invention is to provide the use of equine amniotic membrane-derived mesenchymal stem cells or the tissue cells differentiated therefrom, for cell therapy.

Still another object of the present invention is to provide a method for treating an equine animal, comprising administering the above-described cell therapeutic agent to a subject in need thereof.

Advantageous Effects

According to the present invention, it was found that the equine amniotic membrane can be used as a source of equine mesenchymal stem cells. The equine amniotic membrane-derived mesenchymal stem cells prepared according to the present invention show excellent proliferation and differentiation capabilities, and thus can be used as an active ingredient for a cell therapeutic agent for an equine animal, which requires a large amount of stem cells. Particularly, the stem cells of the present invention, which have excellent growth ability and differentiation capability, can be effectively used for the treatment of bone, tendon, or muscle injuries and loss diseases in racehorses and the like.

DESCRIPTION OF DRAWINGS

FIG. 1 shows the primary culture of equine amniotic membrane-derived mesenchymal stem cells (eAM-MSCs) according to an example of the present invention and is a graphic diagram showing the cumulative population doubling level (CPDL) of the cells. Specifically, FIG. 1A shows an isolated equine amniotic membrane tissue, FIGS. 1B and 1C show phase contrast images of eAM-MSCs, and FIG. 1D shows a cell growth curve of eAM-MSCs.

BEST MODE

Figure 2:
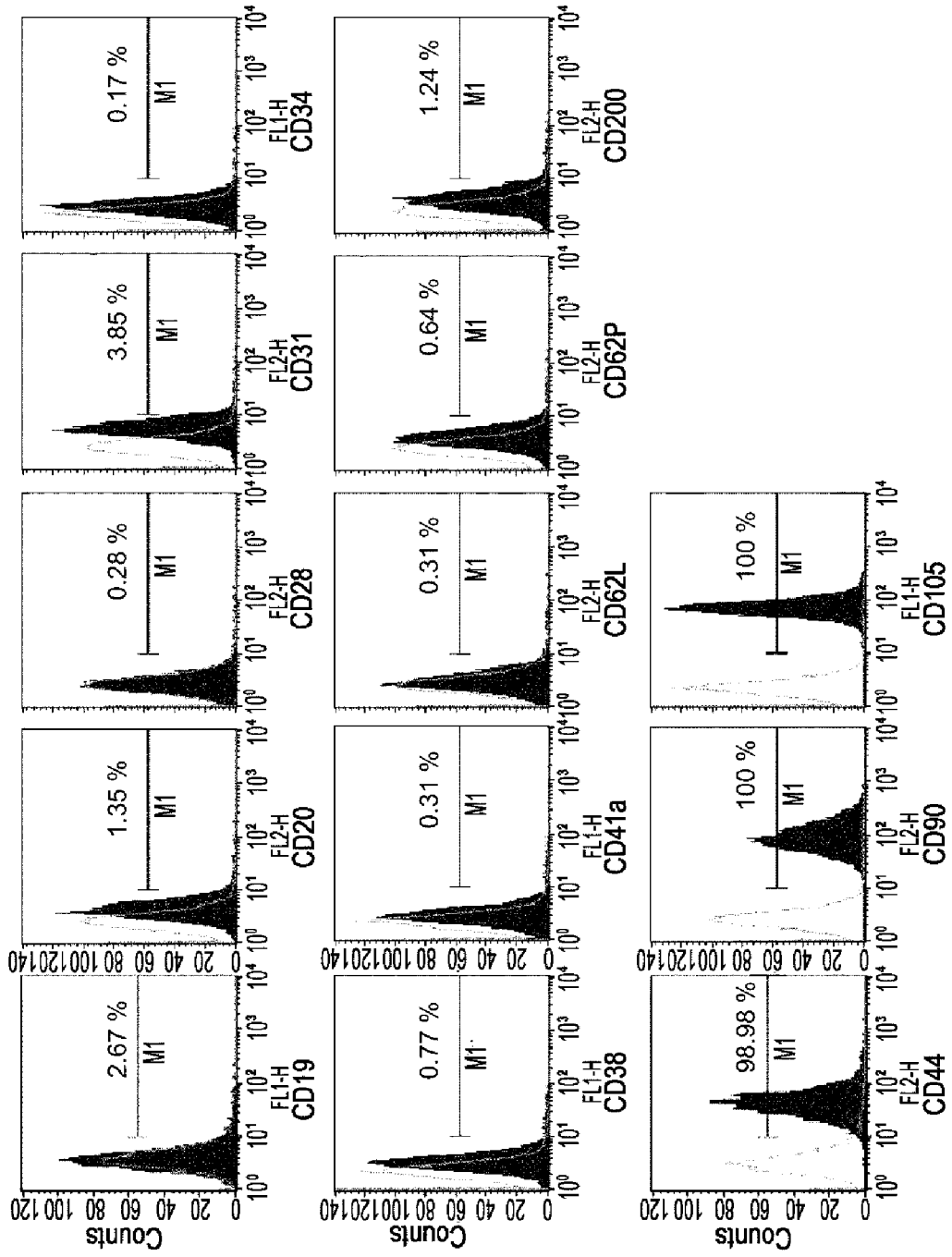
FIG. 2 shows the results of FACS analysis of eAM-MSCs according to an example of the present invention.

In order to accomplish the above objects, an aspect of the present invention provides a method for producing equine amniotic membrane-derived multipotent stem cells, comprising the steps of: (1) isolating cells from an equine amniotic membrane; (2) culturing the isolated cells in low-glucose Dulbecco's modified Eagle medium (LG-DMEM); and (3) harvesting the cultured cells, wherein the equine amniotic membrane-derived multipotent stem cells are characterized by: (a) showing negative immunological responses to all of human markers CD19, CD20, CD28, CD31, CD34, CD38, CD41a, CD62L, CD62P and CD200, and positive immunological responses to all of human markers CD44, CD90 and CD105; (b) having the ability to differentiate into ectoderm, mesoderm or endoderm-derived cells; and (c) having the ability to be maintained in an undifferentiated state for 14 passages or more.

Step (1) is a step of isolating cells from an equine amniotic membrane, which is a source rich in stem cells but which has been disposed of as medical waste. Isolation of the cells is performed by a slight modification of the method known in the art [S. Diaz-Prado et al., *Tissue Eng. Part C Methods*, 2010; C. M. Mihu et al., *Rom. J. Morpho. Embryol.*, 50: 73-77, 2009], and all of placental samples used in the present invention are collected from an equine animal after Cesarean section delivery.

In step (1), before isolating the stem cells, the amniotic membrane is treated with an enzyme to isolate single cells. Preferably, collagenase type I may be used as the enzyme, but the enzyme is not limited thereto.

As used herein, the term "equine animal" refers to a mammal belonging to the family Equidae (Genus *Eauus*). Equine animals together with dogs or cats have been familiar with humans, and all existing horses are all domesticated horses. There is a view that Przewalski's horse (that is currently not found in wild populations) is the ancestor of horses. Young horses are called "foals", and the racehorse industry related to equine animals is growing worldwide. Equine animals belong to a single genus, the genus *Equus*, and include *Equus Grevyi, Equus africanus asinus* (donkeys), *Equus ferus caballus* (horses), *Equus zebra, Equus quagga, Equus hemionus, Equus africanus, Equus kiang*, Tarpan, *Equus ferus przewalskii, Equus hemionus hemippus*, etc.

As used herein, the term "amniotic membrane" refers to a layer that forms a three-layer structure together with chorion and basalis to constitute the placenta. It is a thin, blood vessel-free membrane having a two-layer structure consisting of a simple epithelium and a basement membrane and is a sac that binds to a fetus to constitute an environment. The results of clinical studies indicate that amniotic membrane tissue is effective in wound healing and retinal reconstitution.

As used herein, the term "stem cells" refers to cells having not only self-replication ability but also the ability to differentiate into at least two types of cells. The stem cells can be divided into totipotent stem cells, pluripotent stem cells, and multipotent stem cells (MSCs). In order for cells to be considered as stem cells, the cells must continuously replicate in an undifferentiated state and must be able to differentiate into a specific type of cell under a specific culture condition. Due to their differentiation ability and self-renewal ability, the stem cells described above have recently received attention as a candidate as a composition for cell therapeutic agents, and many studies thereon have been conducted. It was found that equine amniotic membrane-derived multipotent stem cells according to the present invention can proliferate until 14 passages (FIG. 1D).

Figure 3:
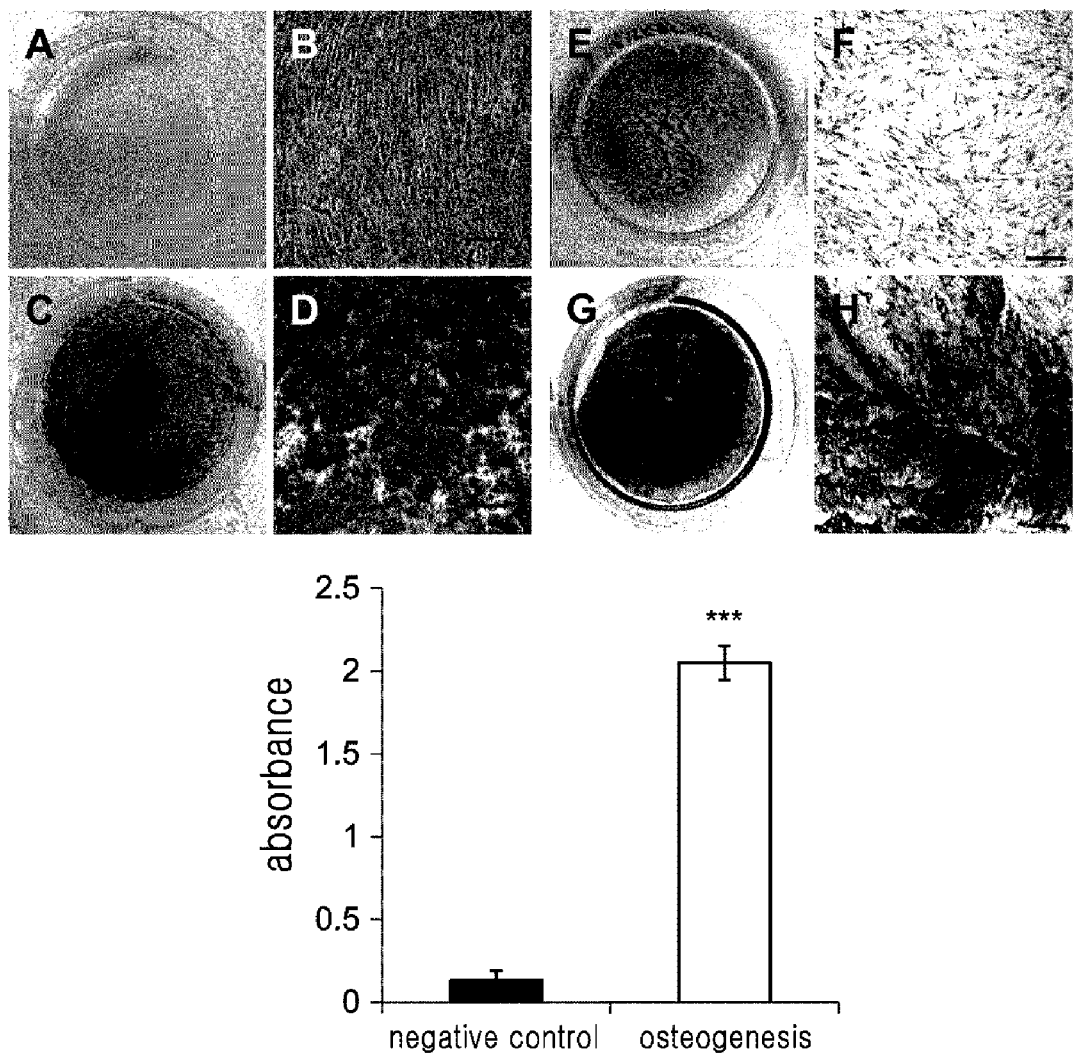
FIG. 3 shows the results of Alizarin Red S staining (A, B, C and D) and von Kossa staining (E, F, G and H), for the induction of osteogenic differentiation of eAM-MSCs according to an example of the present invention, and is a graphic diagram showing the results of quantification of the staining results. Control cells (A, B, E and F) were cultured in low-glucose DMEM medium containing 10% fetal bovine serum.
Figure 4:
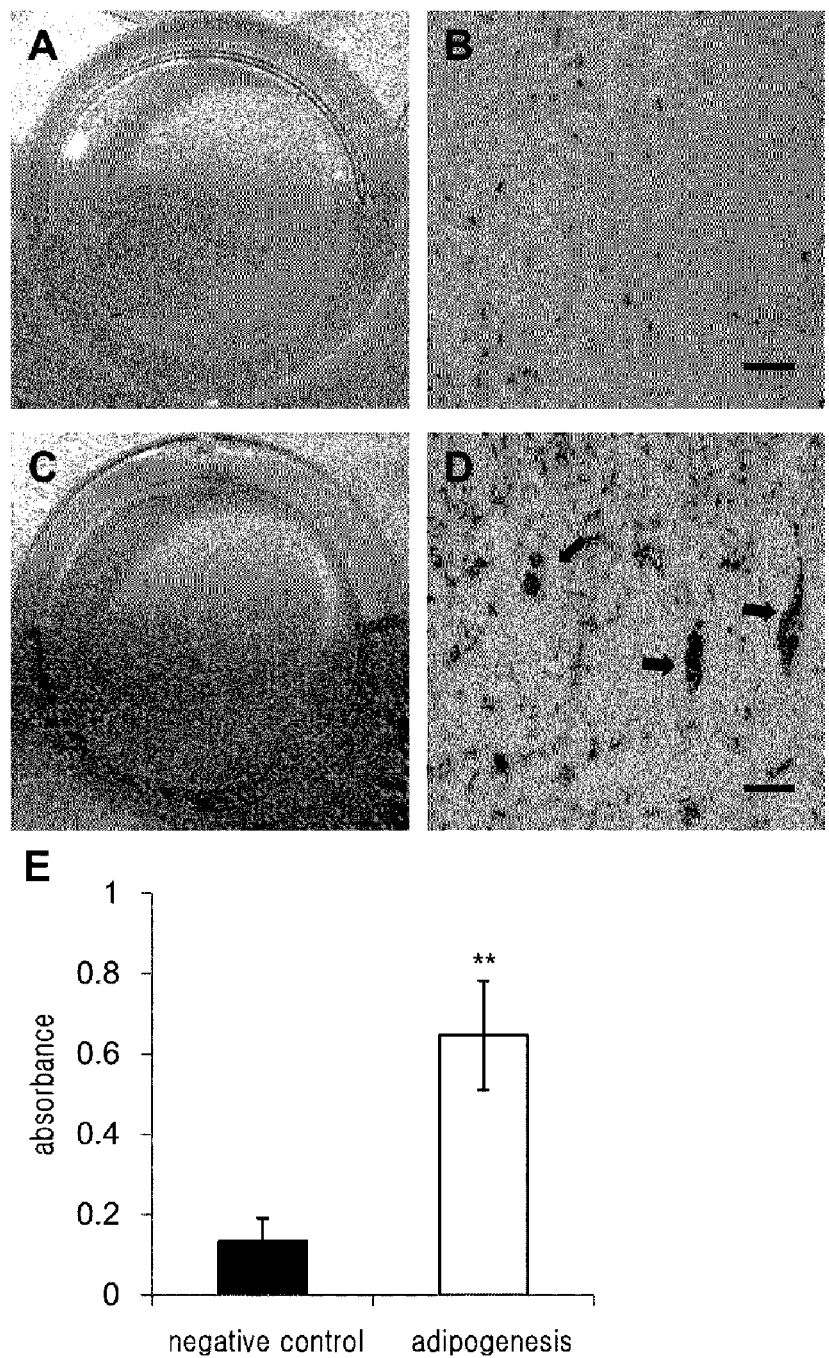
FIG. 4 shows the results of oil red O staining for the induction of adipogenic differentiation of eAM-MSCs according to an example of the present invention (A and B: control groups; C and D: test groups) and is a graphic diagram showing the results of quantification of staining results (E).
Figure 5:
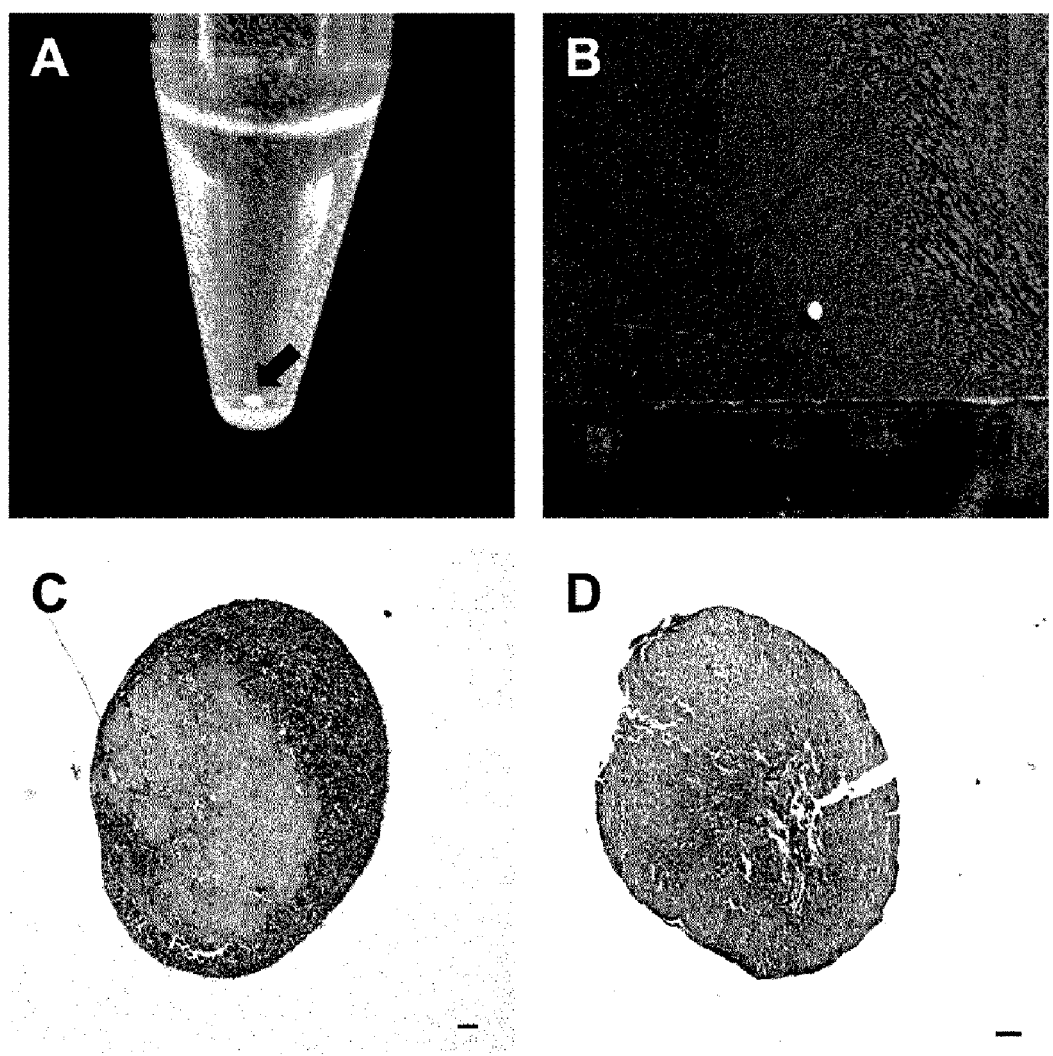
FIG. 5 shows pellet photographs (A and B) and the results of Toluidine blue staining (C) and Alcian blue-PAS staining (D) for the induction of chondrogenic differentiation of eAM-MSCs according to an example of the present invention.

As used herein, the term "multipotent stem cells" refers to cells capable of differentiating only into specific types of cells that form a tissue and organ into which stem cells are introduced. It was found that equine amniotic membrane-derived multipotent stem cells according to the present invention have the ability to differentiate independently into osteocytes, adipocytes or chondrocytes depending on culture conditions (Examples 5 to 7; FIGS. 3 to 5).

Step (2) is a step of culturing the isolated cells in low-glucose Dulbecco's modified Eagle medium (LG-DMEM). In this step, a population of stem cells with increased homogeneity is isolated and allowed to proliferate. The culturing in step (2) is preferably performed in such a manner that the cells adhere to the culture dish. Further, in step (2), the concentration of glucose in the low-glucose DMEM is 800-1200 mg/L, preferably 1000 mg/L. In addition, the low-glucose DMEM medium may contain fetal bovine serum, but is not limited thereto.

The stem cells produced in steps (1) and (2) of the method according to the present invention are characterized by showing negative immunological responses to all of the human markers CD19, CD20, CD28, CD31, CD34, CD38, CD41a, CD62L, CD62P and CD200, and positive immunological responses to all of the human markers CD44, CD90 and CD105. Herein, the human marker CD44 to which the stem cells of the present invention is positive is a cell surface glycoprotein that is involved in the migration of MSCs. The human marker CD90 is also called "Thy-1", which is a marker of several types of stem cells (skin-derived stem cells, endothelium-derived stem cells, and mesenchymal stem cells) [N. M. Masson et al., *Am. J. Physiol. Gastrointest Liver Physiol.*, 290 (1): G45-65, 2006]. Also, the human marker CD105 is also known as endoglin that is a marker of MSCs [M. Dominici et al., *Cytotherapy*, 8 (4): 315-7, 2006]. Meanwhile, the stem cells of the present invention do not have a positive response to the immune cell markers CD19, CD20, CD28, CD38, CD62L and CD200, the endothelial cell markers CD31 and CD62P, the blood cell marker CD34 and the platelet marker CD41a. This suggests that the stem cells produced according to the method of the present invention are multipotent stem cells. Preferably, the multipotent stem cells are mesenchymal stem cells.

According to an example of the present invention, it could be seen that the stem cells produced according to the method of the present invention could differentiate into osteocytes, adipocytes or chondrocytes depending on culture conditions and could proliferate in an undifferentiated state until passage 14. This also suggests that the stem cells produced according to the method of the present invention are multipotent stem cells.

Another aspect of the present invention provides a method for preparing homogeneous equine amniotic membrane-derived multipotent stem cells, comprising isolating mesenchymal stem cells, which show negative immunological responses to all of human markers CD19, CD20, CD28, CD31, CD34, CD38, CD41a, CD62L, CD62P and CD200, and positive immunological responses to all of human markers CD44, CD90 and CD105, from cells isolated from an equine amniotic membrane, wherein the homogeneous equine amniotic membrane-derived multipotent stem cells are characterized by: (a) having the ability to differentiate into ectoderm, mesoderm or endoderm-derived cells; and (b) having the ability to be maintained in an undifferentiated state for 14 passages or more.

Isolation of the cells according to the above-described immunological characteristics is preferably performed using antibodies against the human markers, which show cross-reactivity between different species. Until now, specific antibodies for equine animals have not been found. Thus, in the present invention, the immunological phenotypes of multipotent stem cells isolated from the amniotic membrane are characterized using human-specific antibodies.

A further aspect of the present invention provides equine amniotic membrane-derived multipotent stem cells characterized by: (a) showing negative immunological responses to all of human markers CD19, CD20, CD28, CD31, CD34, CD38, CD41a, CD62L, CD62P and CD200, and positive immunological responses to all of human markers CD44, CD90 and CD105; (b) having the ability to differentiate into ectoderm, mesoderm or endoderm-derived cells; and (c) having the ability to be maintained in an undifferentiated state for 14 passages or more. Preferably, the multipotent stem cells may be mesenchymal stem cells.

A further aspect of the present invention provides a method for differentiating the equine amniotic membrane-derived mesenchymal stem cells into osteocytes, adipocytes or chondrocytes.

In an embodiment, the present invention provides a method for differentiating multipotent stem cells into osteocytes, comprising culturing the equine amniotic membrane-derived multipotent stem cells, produced according to the method of the present invention, in a culture medium comprising ascorbic acid 2-phosphate, dexamethasone and beta-glycerophosphate. Preferably, the culture medium that is used in the culturing may be a osteogenic differentiation medium containing 50 μM ascorbic acid 2-phosphate, 100 nM dexamethasone, 10 mM β-glycerophosphate, and 10% fetal bovine serum in a low glucose-Dulbecco's modified Eagle medium (LG-DMEM), but is not limited thereto.

As used herein, the term "osteocytes" refers to star-shaped cells that are most abundantly present in dense bone tissue and that include a nucleus and a thin cytoplasmic ring. Osteoblasts are trapped in the matrix secreted by themselves and become osteocytes. Osteocytes are networked to each other via long cytoplasmic extensions that occupy tiny canals called canaliculi, which are used for exchange of nutrients and waste through gap junctions. Meanwhile, osteocytes have reduced synthetic activity, are not capable of mitotic division, and develop in mesenchyme, and hydroxyapatite, calcium carbonate and calcium phosphate are deposited around the cell.

In another embodiment, the present invention provides a method for differentiating multipotent stem cells into adipocytes, comprising culturing the equine amniotic membrane-derived multipotent stem cells, produced according to the method of the present invention, in a culture medium containing dexamethasone, indomethacin, 3-isobutyl-1-metyl-xanthine and insulin. Preferably, the medium that is used in the culturing may be an adipogenic differentiation medium containing 1 μM dexamethasone, 60 μM indomethacin, 500 μM 3-isobutyl-1-metyl-xanthine (IBMX) and 5 μg/ml insulin, but is not limited thereto.

As used herein, the term "adipocytes" refers to the cells that primarily compose adipose tissue specialized in storing energy as fat. There are two types of adipose cell: white fat cells that contain a large lipid droplet surrounded by a layer of cytoplasm; and polygonal brown fat cells that have considerable cytoplasm, with lipid droplets scattered throughout. White fat cells secrete proteins acting as adipokines such as resistin, adiponectin and leptin.

In another embodiment, the present invention provides a method for differentiating multipotent stem cells into chondrocytes, comprising culturing the equine amniotic membrane-derived multipotent stem cells, produced according to the method of the present invention, in chondrogenic differentiation medium. Preferably, the method may comprise seeding the cells into a propylene tube, centrifuging the tube to obtain pellets, and culturing the pellets in 1 ml of chondrogenic differentiation medium. The chondrogenic differentiation medium may be a medium containing TGF-β3, dexamethasone, ascorbate and the like, but is not limited thereto, and a commercially available medium may be used.

As used herein, the term "chondrocytes" refers to the only cells found in cartilage. Chondrocytes produce and maintain the cartilaginous matrix composed mainly of collagen and proteoglycan. The organization of chondrocytes in cartilage depends on the shape of cartilage and the location within the tissue.

A further aspect of the present invention provides a cell therapeutic agent, comprising the multipotent stem cells isolated from the equine amniotic membrane according to the method of the present invention, or the cells differentiated therefrom, as an active ingredient.

As used herein, the term "cell therapeutic agent" refers to a drug used for the purpose of treatment, diagnosis and prevention, which contains a cell or tissue prepared through isolation from humans, culture and specific operation (as provided by the US FDA). Specifically, it refers to a drug used for the purpose of treatment, diagnosis and prevention through a series of behaviors of in vitro multiplying and sorting living autologous, allogenic and xenogenic cells or changing the biological characteristics of cells by other means for recovering the functions of cells or tissues.

The cell therapeutic composition of the present invention may further comprise a pharmaceutically acceptable carrier. As used herein, the term "pharmaceutically acceptable" means a carrier that is non-toxic to cells or humans that are exposed to the composition. Examples of carriers that may be used in the present invention include, but are not limited to, buffers, preservatives, analgesics, solubilizing agents, isotonic agents, stabilizers, bases, excipients, lubricants, preservatives and the like. The pharmaceutical composition of the present invention can be formulated in various forms by a conventional technique known in the art. The cell therapeutic agent that is the composition of the present invention may be administered by any route through which it can be delivered to a disease site. In some cases, it can be contemplated to load the cell therapeutic agent into a vehicle comprising a means for delivering stem cells to a lesion. Thus, the composition of the present invention may be administered by various routes, including topical routes (including buccal, sublingual, skin and intraocular routes), parenteral routes (including subcutaneous, intracutaneous, intramuscular, instillation, intravenous, intra-arterial, intra-articular and intra-cerebrospinal routes) or a transdermal route. Preferably, it may be administered parenterally. Most preferably, it is administered directly to a disease site. In an embodiment, the stem cells may be administered to a subject in a state in which these cells are suspended in a suitable diluent at a concentration of about $1 \times 10^3$ to $5 \times 10^6$ cells/ml. Herein, the diluent is used to protect and maintain the cells and to facilitate the injection of the cells into a desired tissue. Examples of the diluent include physiological saline, buffer solution such as phosphate buffered saline or HBSS, plasma, cerebrospinal fluid, or blood components. In addition, the pharmaceutical composition may be administered by any device that can deliver the active ingredient to target cells. Preferred administration mode and formulation are injectable formulations. Injectable formulations can be prepared using aqueous solvents such as physiological saline, Ringer's solution, Hank's solution or sterile aqueous solution, vegetable oils such as olive oil, higher fatty acid esters such as ethyl oleate, or non-aqueous solvents such as ethanol, benzyl alcohol, propylene glycol, polyethylene glycol or glycerin. For transmucous administration, non-invasive agents suitable for a barrier through which the composition is to be passed may be used in formulation. Such non-invasive agents are generally known in the art. In addition, the composition may further comprise pharmaceutically acceptable carriers, including a stabilizer for preventing degeneration (e.g., ascorbic acid, sodium hydrogen sulfite, BHA, tocopherol, EDTA, etc.), an emulsifier, a buffering agent for pH control, and a preservative for inhibiting microbial growth (e.g., phenylmercury nitrate, thimerosal, benzalkonium chloride, phenol, cresol, benzylalcohol, etc.).

Preferably, the cell therapeutic agent may be used for the treatment of equine osteoarthritis, for the treatment of equine bone loss disease, for the formation of equine adipose tissue, for the formation of equine tendon tissue, or for the formation of equine muscle tissue.

Therefore, the present invention provides the use of equine amniotic membrane-derived mesenchymal stem cells or tissue cells differentiated therefrom, for cell therapy.

The present invention also provides a method for treating an equine animal, comprising administering the cell therapeutic agent to a subject in need thereof.

As used herein, the term "treating" refers to all actions that alleviate or beneficially change symptoms of an equine disease, for example, a disease caused by the injury or loss of muscle, cartilage or adipose tissue, by administering the composition of the present invention.

Mode for Invention

Hereinafter, the present invention will be described in more detail with reference to Examples. However, these Examples are for illustrative purposes only, and the invention is not intended to be limited by these Examples.

The present invention was conducted in accordance with "the Guide for the Care and Use of Laboratory Animals" of Seoul National University (Korea), and performed in accordance with the policies and regulations of organizations and governments, which are applicable to the ethical use of animals.

Moreover, statistical analysis in all of the following Examples was performed using Stat View software package (SAS, Cary, N.C.). Data were expressed as mean±S.E.M from five or more independent experiments. Statistically significant differences between groups were calculated from repeated measures of ANOVA test.

Example 1: Collection of Equine Amniotic Membrane

Amniotic membranes, which were normally disposed of after separation by Cesarean section delivery, were used (the College of Veterinary Medicine, Seoul National University). These membranes were for research purposes only and were provided without cost. The separated membranes were used only for the isolation and characterization of stem cells from the tissue.

All placental samples (n=4) were obtained from pure-bred female horses after delivery in Korean private horse farms. In order to reduce the contamination and damage of the tissue, all the samples were collected immediately after delivery using sterile surgical tools. The collected placental samples were stored at 4° C. and transferred to the laboratory as soon as possible in order to avoid possible contamination from a dusty environment. The amniotic membrane was physically separated from the chorion.

Example 2: Isolation and Culture of Stem Cells

Cell isolation and culture were performed by a slight modification of the previously described method [S. Diaz-Prado et al., *Tissue Eng. Part C Methods*, 2010; C. M. Mihu et al., *Rom. J. Morpho. Embryol*, 50: 73-77, 2009]. All the placental samples were collected from equine animals through Cesarean section delivery by the method of Example 1. To separate the amniotic membrane from the whole placenta, the amniotic membrane was physically separated from the chorion. Under sterile conditions, the collected amniotic membrane was washed 3-4 times with physiological saline (0.9%). To remove epithelial cells, the collected amniotic membrane was treated with trypsin-EDTA (0.25%) at 37° C. for 30 minutes and washed 3-4 times with physiological saline. Then, the amniotic membrane from which epithelial cells were removed was cut into small pieces with a surgical knife and treated with collagenase type I (2 mg/ml; Worthington biochemical, Freehold, N.J.) at 37° C. for about 3-4 hours to separate into single mesodermal cells. Then, the cells were washed with phosphate buffered saline (PBS; Cellgro, USA) by centrifugation at 350 g for 5 minutes. After removing the supernatant, the cell pellets were re-suspended in 10% FBS-containing low-glucose DMEM (LG-DMEM; Gibco BRL, USA), a basal medium. The cells were seeded into a 75T polystyrene culture flask (Nunc, USA) and incubated in a 5% $CO_2$ humidified incubator. The basal medium was replaced three times a week, and when a confluence of 80-90% was reached, the cells were subcultured.

The results of the culture are shown in FIG. 1. FIG. 1A shows the amniotic membrane separated from the equine placental tissue. eAM-MSCs isolated from the amniotic membrane showed the typical pyramidal shape of MSCs and adhered to the plastic culture dish (FIGS. 1B and 1C).

Example 3: Cumulative Population Doubling Level Analysis

The analysis of cell proliferation was performed by a slight modification of the previously described method [S. B. Park et al., *Cytotherapy*, 13: 1431-43, 2011]. Stem cells, including multipotent stem cells, have self-renewal capacity which is associated with continuous and steady proliferation rate [Reya T. et al., *Nature*, 414 (6859): 105-11, 2001]. Therefore, the estimated growth efficiency and proliferation potential of the eAM-MSCs obtained in Example 2 were determined based on the total cumulative population doubling level using the formula CPDL=ln (Nf/Ni) ln 2, wherein Ni is the initial seeding cell number, Nf is the final harvesting cell number, and ln is the natural log. The cells ($5 \times 10^4$) were seeded into three 6-well culture plates, and after 5-7 days, subcultured. The number of final cells was counted, and $5 \times 10^4$ cells were re-seeded. To determine the cumulative population doubling level, the population doubling level of each passage was calculated and added to the previous population doubling level. This procedure was repeated until passage 14 where the proliferation rate started to decrease.

As a result, as shown in FIG. 1D, a steady increase in cell growth was observed up to passage 14. Steady cell proliferation ability is associated with the characteristics of stem cells. Stem cells have self-renewal ability, which is associated with continuous and steady cell proliferation. Thus, these CPDL results demonstrate that the isolated eAM-MSCs have self-renewal ability.

Example 4: Immunotypic Characterization of eAM-MSCs by Flow Cytometry

Cells were stained for flow cytometry with specific antibodies according to the manufacturer's protocol (BD Biosciences, USA). Briefly, the cultured eAM-MSCs were washed twice with PBS and harvested using 0.25% trypsin/EDTA. Then, the cells were washed with PBS and divided into groups for antibody staining. Each divided group contained about $1 \times 10^5$ cells. The following antibodies were used for cell surface antigen detection: mouse anti-human CD19, mouse anti-human CD20, mouse anti-human CD28, mouse anti-human CD31, mouse anti-human CD34, mouse anti-human CD38, mouse anti-human CD41a, mouse anti-human CD44, mouse anti-human CD62L, mouse anti-human CD62P, mouse anti-human CD90, mouse anti-human CD200 (BD Biosciences) and mouse anti-human CD105 (Serotec, USA). All the antibodies were conjugated to fluorescein isothiocyanate (FITC) or phycoerythrin (PE). The cells were stained at 4° C. for 30 minutes. After treatment at constant temperature, the cells were washed with PBS and re-suspended in 500 μl of PBS. Analysis was carried out with a FACS Calibur™ (BD Biosciences) and Cell Quest Pro™ (BD Biosciences) software.

Generally, MSCs show the unique patterns of cell surface antigens, including CD44, CD90 and CD105. However, MSCs show negative responses to CD11b, CD14, CD19, CD79a, CD34, CD45 and HLA-DR [M. Dominici et al., Cytotherapy, 8 (4): 315-7, 2006]. The present inventors conducted flow cytometry of eAM-MSCs at passage 5 using 13 CD markers (CD19, CD20, CD28, CD31, CD34, CD38, CD41a, CD44, CD62L, CD62P, CD90, CD105 and CD200) to determine whether these cells show the characteristics of MSCs (FIG. 2). The eAM-MSCs expressed CD44, CD90 and CD105. CD44 is a cell-surface glycoprotein that is involved in the migration of MSCs. CD90, also called Thy-1, is a marker of several types of stem cells, including hepatic stem cells, ketatinocyte stem cells, uterine endometrium stem cells and mesenchymal stem cells. CD105, also called SH2, is a well known marker of MSCs. The eAM-MSCs did not express other markers such as those that are expressed in immune cells (CD19, CD20, CD28, CD38, CD62L and CD200), endothelial cells (CD31 and CD62P), hematopoietic stem cells (CD34) and platelet (CD41a). These results indicate that eAM-MSCs have immunological characteristics similar to those of general MSCs.

Example 5: Possibility of Differentiation into Osteocytes

In order to test the osteogenic ability of the eAM-MSCs produced in Example 2, the cells were treated with an osteogenic differentiation medium containing ascorbic acid 2-phosphate (50 μM), dexamethasone (100 nM), β-glycerophosphate (10 mM; Sigma-Aldrich, USA) and 10% fetal bovine serum (FBS) in low-glucose Dulbecco's modified Eagle medium (LG-DMEM). As a control, a basal medium was used. eAM-MSCs ($1 \times 10^5$) were seeded into three 6-well plates. When the cells reached a confluence of 80-90%, the medium was replaced with osteogenic differentiation medium. The cells were maintained in fresh medium for 3 weeks. The differentiation medium was replaced twice a week. After differentiation, Alizarin Red S staining and von Kossa staining were performed to detect calcium deposition. Briefly, for Alizarin Red S staining, the cells were washed with PBS and fixed with ice-cold 70% ethanol at 4° C. for 1 hour. Then, the cells were rinsed 3-4 times with distilled water. Staining was performed with Alizarin Red S (40 mM; pH 4.2; Sigma-Aldrich, USA) at room temperature for 10 minutes. To remove non-specific stains, the cells were rinsed with distilled water. For von Kossa staining, the cells were stained with 5% silver nitrate for 30-60 minutes under exposure to UV rays, and then treated with 5% sodium thiosulfate for 2-3 minutes, after which the cells were counter-stained with nuclear red for 5 minutes. The Alizarin Red S stain was solubilized using cetylpyridinium chloride (100 mM; Sigma-Aldrich) for 1 hour. The absorbance of the solubilized Alizarin Red S was measured at 570 nm using a spectrophotometer.

As a result, in the control group under the basal culture conditions, the stem cells were negative for Alizarin Red S staining and von Kossa staining (FIGS. 3A, 3B, 3E and 3F), whereas, when the stem cells were treated with the osteogenic differentiation medium, the stem cells showed strong positive responses to Alizarin Red S staining and von Kossa staining (FIGS. 3C, 3D, 3G and 3H). For quantification, the absorbance of the Alizarin Red S solubilized using cetylpyridinium chloride was about 15 times higher in the differentiated cells than in the control group (FIG. 3I).

Example 6: Possibility of Differentiation into Adipocytes

In order to test the adipogenic differentiation ability of the eAM-MSCs produced in Example 2, the eAM-MSCs were treated with an adipogenic differentiation medium containing dexamethasone (1 μM), indomethacin (60 μM), 3-isobutyl-1-methylxanthine (500 μM; IBMX) and insulin (5 μg/ml; Sigma-Aldrich, USA) in 10% FBS-containing LG-DMEM. As a control, a basal culture medium was used. When the cells reached a confluence of 80-90%, the cells were treated with an adipogenic differentiation medium for 3 weeks. The medium was replaced twice a week. After differentiation, oil red O staining was performed to detect lipid drops. The cells were fixed by incubation in 10% formalin for at least 1 hour at a constant temperature, and then rinsed with 60% isopropanol prior to incubation in freshly diluted Oil Red O for 10 minutes at a constant temperature. The stain was solubilized with 100% isopropanol, and the absorbance of the solubilized stain was measured at 570 nm using a spectrophotometer.

As a result, lipid drops formed under the differentiation conditions could be detected (FIGS. 4C and 4D), and no lipid drop was detected in the control conditions (FIGS. 4A and 4B). In order to quantify the differentiation state of the cells, the oil red O stain was eluted, and the absorbance thereof was measured and the results of the measurement are shown in FIG. 4E. As can be seen therein, the absorbance of the differentiated cells was 5 times higher than that of the control cells.

Example 7: Possibility of Differentiation into Chondrocytes

In order to test the chondrogenic ability of the eAM-MSCs produced in Example 2, the eAM-MSCs were treated with a chondrogenic differentiation medium. As a control, a basal culture medium was used. The cells ($5 \times 10^5$) were seeded into a 15 mL polypropylene tube and centrifuged to obtain pellets. The pellets were cultured in 1 ml of chondrogenic differentiation medium (Lonza) and incubated in a 5% $CO_2$ incubator at 37° C. for 3 weeks at a constant temperature. The medium was replaced every 3-day. After differentiation, the pellets were embedded in paraffin and cut into 3-mm sections. To detect chondrogenesis, the sections were stained with toluidine blue and Alcian blue-PAS to detect chondrogenesis according to standard protocols. Briefly, a slice of the 3 mm cell pellet mounted on a slide was deparaffinized and hydrated with distilled water. For toluidine blue staining, the slide was immersed in a toluidine blue working solution for 1 minute. An excess of unbound stain was washed out several times with distilled water. The slide was quickly dehydrated by successive washing with 95% and absolute alcohol. For Alcian blue-PAS staining, the slide was stained with Alcian blue (pH 2.5), 0.5% periodic acid and Schiff reagent. The slide was cleaned with xylene, and then covered with with Canada balsam and a coverslip.

As a result, after 3 weeks of differentiation, the formation of a pellet in the bottom of the polypropylene tube was observed. The pellet was oval in shape and was opaque (FIGS. 5A and 5B). The black arrow indicates the formation of the pellet (FIG. 5A). However, under the control conditions, no pellet formation was observed. When the medium was replaced, the cells were re-suspended, suggesting that chondrogenesis did not occur in the basal medium. The pellet was positively stained with toluidine blue (FIG. 5C) and Alcian blue-PAS (FIG. 5D).

The invention claimed is:

1. A method for producing equine amniotic membrane-derived multipotent stem cells comprising the steps of:
    (1) isolating cells from an equine amniotic membrane;
    (2) culturing the isolated cells in low glucose Dulbecco's modified Eagle medium (LG-DMEM); and
    (3) harvesting the cultured cells,
    wherein the equine amniotic membrane-derived multipotent stem cells cultured by the step (2) are selected for:
    (a) showing negative immunological responses to all of human markers CD19, CD20, CD28, CD31, CD34, CD38, CD41a, CD62L, CD62P and CD200, and positive immunological responses to all of human markers CD44, CD90 and CD105; and
    (b) having the ability to be maintained in an undifferentiated state for 14 passages or more.

2. The method of claim 1, wherein step (1) comprises the sub-steps:
    (i) degrading the amniotic membrane with an enzyme to remove an amniotic epithelial cell layer; and
    (ii) isolating single mesodermal cells from the amniotic membrane, from which the amniotic epithelial cell layer was removed, by a chemical method.

3. The method of claim 2, wherein the enzyme in sub-step (i) is trypsin-EDTA.

4. The method of claim 2, wherein the chemical method in sub-step (ii) is a treatment with collagenase type I.

5. The method of claim 1, wherein step (2) is performed by adherent culture.

6. The method of claim 1, wherein the LG-DMEM in the step (2) has a glucose concentration of 800-1200 mg/L.

7. The method of claim 1, wherein the LG-DMEM in the step (2) contains fetal bovine serum.

8. The method of claim 1, wherein the equine is selected from the group consisting of subgenus *Hippotigris*, subgenus *Equus*, mule, and subgenus *Asinus*.

9. The method of claim 1, wherein the multipotent stem cells are mesenchymal stem cells.

10. A method for differentiating multipotent stem cells into osteocytes, comprising culturing the multipotent stem cells prepared by the method of claim 1, in a culture medium comprising ascorbic acid 2-phosphate, dexamethasone and beta-glycerophosphate.

11. A method for differentiating multipotent stem cells into adipocytes, comprising culturing the multipotent stem cells prepared by the method of claim 1, in a culture medium comprising dexamethasone indomethacin, 3-isobutyl-1-methyl-xanthine, and insulin.

12. A method for differentiating multipotent stem cells into chondrocytes, comprising culturing the multipotent stem cells prepared by the method of claim 1, in a chondrogenic differentiation medium.

13. A method for treating an equine animal, comprising the steps of:
    (1) isolating cells from an equine amniotic membrane;
    (2) culturing the isolated cells in low glucose Dulbecco's modified Eagle medium (LG-DMEM); and
    (3) harvesting the cultured cells; and
    (4) administering the harvested cells to a subject in need thereof, wherein the equine amniotic membrane-derived multipotent stem cells cultured by the step (2) are selected for:
    (a) showing negative immunological responses to all of human markers CD19, CD20, CD28, CD31, CD34, CD38, CD41a, CD62L, CD62P and CD200, and positive immunological responses to all of human markers CD44, CD90 and CD105; and
    (b) having the ability to be maintained in an undifferentiated state for 14 passages or more.

14. The method of claim 13, wherein the subject in need is treated for equine arthritis, equine bone loss disease, formation of equine adipose tissue, formation of equine tendon tissue, or for formation of equine muscle tissue.

* * * * *